(12) United States Patent
Takeuchi et al.

(10) Patent No.: US 8,354,382 B2
(45) Date of Patent: Jan. 15, 2013

(54) HEMIFUMARATE OF A PYRAZOLE DERIVATIVE

(75) Inventors: Hideki Takeuchi, Joetsu (JP); Eiji Tsuru, Joetsu (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 190 days.

(21) Appl. No.: 12/988,273

(22) PCT Filed: Apr. 13, 2009

(86) PCT No.: PCT/JP2009/057439
§ 371 (c)(1), (2), (4) Date: Oct. 15, 2010

(87) PCT Pub. No.: WO2009/128421
PCT Pub. Date: Oct. 22, 2009

(65) Prior Publication Data
US 2011/0034679 A1 Feb. 10, 2011

(30) Foreign Application Priority Data
Apr. 16, 2008 (JP) ................. 2008-106582

(51) Int. Cl.
*A01N 43/04* (2006.01)
*A61K 31/70* (2006.01)
*C07G 3/00* (2006.01)
*C07H 15/00* (2006.01)
*C07H 17/00* (2006.01)
*C07H 17/02* (2006.01)
*C07H 23/00* (2006.01)

(52) U.S. Cl. ............ 514/27; 514/25; 536/4.1; 536/17.2; 536/17.3; 536/17.4

(58) Field of Classification Search .................. None
See application file for complete search history.

(56) References Cited

U.S. PATENT DOCUMENTS

| 7,635,684 B2 * | 12/2009 | Fushimi et al. ............... 514/27 |
| 2003/0195343 A1 | 10/2003 | Shimizu et al. |
| 2005/0124681 A1 | 6/2005 | Schubert et al. |
| 2005/0272669 A1 | 12/2005 | Fushimi et al. |

FOREIGN PATENT DOCUMENTS

| JP | 2003-517468 A | 5/2003 |
| JP | 2007-513243 A | 6/2007 |
| WO | 01/34586 A2 | 5/2001 |
| WO | 02/018403 A1 | 3/2002 |
| WO | 2004/018491 A1 | 3/2004 |
| WO | 2007/080170 A1 | 7/2007 |

OTHER PUBLICATIONS

Adachi et al., Metabolism, vol. 49, No. 8, 2000, 990-995.*
Mayo Clinic Staff, "type 1 diabetes"; also available at http://www.mayoclinic.com/health/type-1-diabetes/DS00329; last viewed Jun. 17, 2012.*
International Search Report, PCT/JP2009/057439 dated Jun. 30, 2009.

* cited by examiner

*Primary Examiner* — Traviss C McIntoshi, III
(74) *Attorney, Agent, or Firm* — Sughrue Mion, PLLC

(57) ABSTRACT

The present invention provides a novel form of 3-(3-{4-[3-(β-D-glucopyranosyloxy)-5-isopropyl-1H-pyrazol-4-ylmethyl]-3-methylphenoxy}propylamino)-2,2-dimethylpropionamide with improved storage stability. Since 3-(3-{4-[3-(β-D-glucopyranosyloxy)-5-isopropyl-1H-pyrazol-4-ylmethyl]-3-methylphenoxy}-propylamino)-2,2-dimethylpropionamide hemifumarate dihydrate has extremely excellent storage stability, it is useful as a drug substance. Furthermore, it shows an extremely good crystalline property and can be purified by a convenient method, and therefore is suitable for the industrial preparation.

7 Claims, 5 Drawing Sheets

HEMIFUMARATE OF A PYRAZOLE DERIVATIVE

CROSS REFERENCE TO RELATED APPLICATIONS

This application is a National Stage of International Application No. PCT/JP2009/057439, filed on Apr. 13, 2009, which claims priority from Japanese Patent Application No. 2008-106582 filed on Apr. 16, 2008, the contents of all of which are incorporated herein by reference in their entirety.

TECHNICAL FIELD

The present invention relates to a compound (chemical name: 3-(3-{4-[3-(β-glucopyranosyloxy)-5-isopropyl-1H-pyrazol-4-ylmethyl]-3-methylphenoxy}-propylamino)-2,2-dimethylpropionamide hemifumarate dihydrate; hereinafter sometimes to be abbreviated as the "hemifumarate dihydrate") represented by the formula:

[Chem. 1]

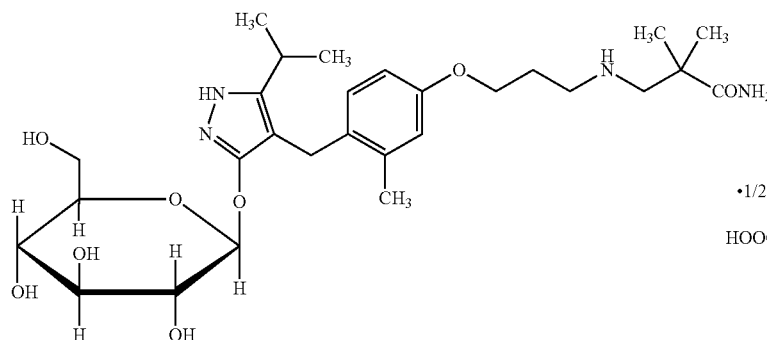

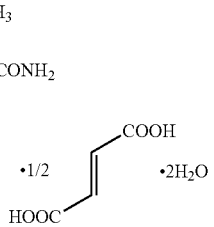

(A)

which exhibits an inhibitory activity in human SGLT1 and is useful as an agent for the prevention or treatment of a disease associated with hyperglycemia such as diabetes, impaired glucose tolerance, impaired fasting glycemia, diabetic complications or obesity, and a disease associated with the increase in blood galactose level such as galactosemia.

BACKGROUND ART

Although a compound represented by the formula:

[Chem. 2]

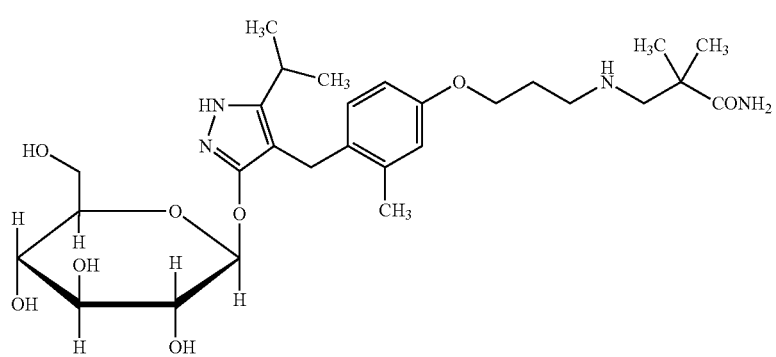

(B)

which exhibits an inhibitory activity in human SGLT1 and is useful as an agent for the prevention or treatment of a disease associated with hyperglycemia such as diabetes, impaired glucose tolerance, impaired fasting glycemia, diabetic complications or obesity, and a disease associated with the increase in blood galactose level such as galactosemia is disclosed (see Patent reference 1), any concrete salts of the compound have not been reported.

Patent reference 1: International publication pamphlet No. 2004/018491

DISCLOSURE OF THE INVENTION

Objects to be Solved by the Invention

The compound (B) described in Patent reference 1 is amorphous material. As described in Test Examples mentioned below (Storage Stability Tests), the decrease in the purity due to decomposition of the compound and the deliquescence were observed. Because of bad storage stability, it is required to make improvement in the physicochemical property to use the compound (B) as a drug substance.

An objective of the present invention is to provide a different form from the above compound (B), which has high storage stability and is usable for a drug substance.

Means of Solving the Objects

The present inventors have earnestly studied to solve the above objective. As a result, the present inventors found that 3-(3-{4-[3-(β-D-glucopyranosyloxy)-5-isopropyl-1H-pyrazol-4-ylmethyl]-3-methylphenoxy}propylamino)-2,2-dimethyl-propionamide hemifumarate dihydrate has extremely excellent storage stability and extremely good crystalline property and is suitable for the industrial preparation, and therefore is suitable for a drug substance, thereby accomplished the present invention.

That is, the present invention relates to:

[1] a compound represented by the above chemical structural formula (A);
[2] the compound as described in the above [1], which is crystalline;
[3] the compound as described in the above [2], which has characteristic peaks at diffraction angles (2θ(°)) of 7.6±0.1, 10.8±0.1, 13.0±0.1, 13.3±0.1, 22.9±0.1 and 27.2±0.1 in a diagram of the powder X-ray diffraction;
[4] the compound as described in the above [2], which has endothermic peaks at around 76° C. and around 129° C. in a chart of the differential thermal;
[5] the compound as described in the above [2], which has characteristic peaks at chemical shift values (δ (ppm)) of 132.8±0.2, 102.3±0.2, 76.9±0.2 and 26.9±0.2 in a chart of the solid-state $^{13}$C-NMR spectrum;
[6] a pharmaceutical composition which comprises as an active ingredient a compound as described in any one of the above [1] to [5];
[7] the pharmaceutical composition as described in the above [6], for the prevention or treatment of a disease associated with hyperglycemia or a disease associated with the increase in blood galactose level;
[8] a medicament which comprises a compound as described in any one of the above [1] to [5] in combination with any one of sulfonylureas and glinides;
[9] the medicament as described in the above [8], which comprises a compound as described in any one of the above [1] to [5] in combination with either gliclazide or mitiglinide calcium hydrate;
[10] the medicament as described in the above [8] or [9], for the prevention or treatment of a disease associated with hyperglycemia; and the like.

Effects of the Invention

The hemifumarate dihydrate of the present invention does not deliquesce in long storage and shows almost no decrease in the purity, and therefore has excellent storage stability. In addition, the hemifumarate dihydrate has an extremely good crystalline property and is excellent in fluidity. Thus, for example, the hemifumarate dihydrate is easy to use for formulation. Furthermore, since the hemifumarate dihydrate can be purified in high purity by a convenient method, it is suitable for the industrial preparation.

BEST MODE FOR CARRYING OUT THE INVENTION

The hemifumarate dihydrate of the present invention can be prepared, for example, by a method described below.

That is, the hemifumarate dihydrate can be obtained by mixing the above compound (B), which can be prepared by a method described in Patent reference 1 or a similar method thereto, and ½ equivalents of fumaric acid in an appropriate good solvent, dissolving the mixture by heating and optionally adding an appropriate poor solvent thereto, and subsequently isolating the hemifumarate precipitated by cooling to stand, under water cooling or around room temperature. In this case, the hemifumarate is obtained as a solvate crystal with a solvent to use (for example, when ethanol is used, ethanol solvate crystal is obtained), and the crystal of hemifumarate dihydrate can be prepared by storing the solvate crystal under humidification.

The good solvents include any solvent which does not interfere with salt formation, and for example, alcohols such as methanol, ethanol, 1-propanol or the like, water or the like can be used. In addition, the good solvents may be used as a mixture of two or more good solvents.

As the poor solvents, for example, carboxylic acid esters such as ethyl acetate or the like, hydrocarbons such as heptane, toluene or the like, ethers such as diisopropyl ether, diethyl ether, tert-butylmethyl ether or the like, ketones such as methylethylketone or the like, or acetonitrile or the like can be used. In addition, the poor solvents may be used as a mixture of two or more poor solvents.

The hemifumarate dihydrate of the present invention can be optionally purified by recrystallizing the hemifumarate dihydrate which is prepared by the above method and the like using an appropriate recrystallization solvent such as ethanol-diisopropyl ether mixed solvent, ethanol-toluene mixed solvent, ethanol-water mixed solvent, methanol-diisopropyl ether mixed solvent, methanol-ethyl acetate mixed solvent or the like.

In the Storage Stability Test as described below, since the deliquescence from the initial point of the experiment was observed in the 3-(3-{4-[3-(β-D-glucopyranosyloxy)-5-isopropyl-1H-pyrazol-4-ylmethyl]-3-methylphenoxy}propylamino)-2,2-dimethylpropionamide ¾ fumarate dihydrate (hereinafter sometimes to be abbreviated as the "¾ fumarate dihydrate") of Comparative Example 1 as crystalline, furthermore, the remarkable decrease in the purity accompanied with the deliquescence was observed in the above compound (B) as amorphous, these compounds have a problem of stability. However, unlike ¾ fumarate dihydrate and the like, the hemifumarate dihydrate of the present invention showed no deliquescence and no remarkable decrease in the purity and had extremely excellent storage stability. Thus the hemifumarate dihydrate has high storage stability and is usable for a drug substance.

The hemifumarate dihydrate of the present invention is useful as an agent for the prevention or treatment of a disease associated with hyperglycemia or a disease associated with the increase in blood galactose level. In the present invention, as a disease associated with hyperglycemia, diabetes, impaired glucose tolerance, impaired fasting glycemia, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia, gout and the like can be illustrated. In addition, as a disease associated with the increase in blood galactose level, galactosemia and the like can be illustrated.

A pharmaceutical composition of the present invention can be prepared by suitably admixing the hemifumarate dihydrate with a pharmaceutical carrier used conventionally as a pharmaceutical additive such as excipients, disintegrating agents, binders, lubricants, diluents, buffer agents, tonicity agents, antiseptics, moistening agents, emulsifying agents, dispersing agents, stabilizing agents, dissolving aids and the like.

In the case of employing a pharmaceutical composition of the present invention for the practical treatment, various dosage forms can be administered depending upon their usages. As the dosage forms, for example, powders, granules, fine granules, dry syrups, tablets, capsules, injections and the like can be illustrated and they are orally or parenterally administered. The dosage of the hemifumarate dihydrate is appropriately decided depending on the age, sex, body weight, and the degree of symptoms and treatment of each patient and the like, which is within the range of from about 0.01 mg to about 1000 mg per day per adult human in the case of oral administration and within the range of from about 0.001 mg to about 300 mg per day per adult human in the case of parenteral administration. The daily dose can be divided into one to several doses and administered suitably.

The compound of the present invention can be used in combination with any one of sulfonylureas or glinides. As sulfonylureas, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride and the like can be illustrated. As glinides, nateglinide, mitiglinide calcium hydrate, repaglinide and the like can be illustrated. The dosage of each drug is appropriately decided depending on the age, sex, body weight, and the degree of symptoms and treatment of each patient and the like, according to each effective dose.

In the case of using the compound of the present invention in combination with any one of sulfonylureas or glinides, the present invention includes either dosage forms of simultaneous administration as a single preparation or separated preparations in way of the same or different administration route, and administration at different dosage intervals as separated preparations in way of the same or different administration route. A medicament comprising the compound of the present invention in combination with any one of sulfonylureas or glinides includes both dosage forms as a single preparation and separated preparations for the combination as mentioned above.

EXAMPLES

The present invention is further illustrated in more detail by way of the following Examples and Test Examples. However, the present invention is not limited thereto.

Example 1

3-(3-{4-[3-(β-D-Glucopyranosyloxy)-5-isopropyl-1H-pyrazol-4-ylmethyl]-3-methylphenoxy}propylamino)-2,2-dimethylpropionamide hemifumarate dihydrate 3-(3-{4-[3-(β-D-Glucopyanosyloxy)-5-isopropyl-1H-pyazol-4-ylmethyl]-3-methylphenoxy}propylamino)-2,2-dimethylpropionamide (17 g) was dissolved in ethanol (150 mL) by heating at 40° C., ½ equivalents of fumaric acid (1.75 g) and the ethanol (105 mL) was added to the solution, and the mixture was stirred under heating at 70° C. After cooling to room temperature, the mixture was stirred for 2 hours. The precipitates were collected by filtration, the resulting precipitates were dried at 70° C. for 12 hours under reduced pressure, and the crystals of hemifumarate ethanol solvate (18.5 g) were obtained.

The crystals of hemifumarate ethanol solvate (6.4 g) were dissolved in a mixed solvent of ethanol (64 mL) and water (3.2 mL) under heating at 60° C. Insoluble materials were filtered off, and the filtrate was stirred under room temperature for 15 hours. The precipitated crystals were collected by filtration and dried at 50° C. under reduced pressure. The resulting crystals were allowed to stand under 25° C. and 60% relative humidity for 2 days, and moreover, under 40° C. and 75% relative humidity for 7 days, and the crystals of hemifumarate hydrate (5.3 g) were obtained.

$^1$H-NMR (DMSO-$d_6$) (δ (ppm)): 1.00-1.10 (12H, m), 1.88 (2H, t, J=6.5 Hz), 2.26 (3H, s), 2.64 (2H, s), 2.70-2.80 (3H, m), 3.10-3.30 (4H, m), 3.40-3.60 (3H, m), 3.62 (1H, d, J=11.0 Hz), 3.95 (2H, t, J=6.0 Hz), 4.40-4.60 (1H, br), 5.18 (1H, d, J=7.5 Hz), 6.47 (1H, s), 6.61 (1H, d, J=7.5 Hz), 6.70 (1H, s), 6.82 (1H, d, J=8.5 Hz), 6.89 (1H, s), 7.50 (1H, s), 11.00-12.00 (1H, br)

The powder X-ray diffraction, differential thermal analysis/thermogravimetry, infrared absorption spectroscopy and solid-state $^{13}$C-NMR spectrum of the obtained hemifumarate dihydrate crystals were measured under the following conditions and respective data were obtained.

The powder X-ray diffraction was measured using RINT2100 X-ray diffractometer (Rigaku, Analytical condition: Cu Kα radiation, 40 kV in tube voltage, and 40 mA in tube current). The resulting diffraction diagram is shown in FIG. 1, and the diffraction angles 2θ(°) and relative intensities (%) of the main peaks are shown in Table 1.

TABLE 1

| Diffraction angle (2θ (°)) | Relative intensity (%) |
| --- | --- |
| 7.6 | 100 |
| 9.2 | 10 |
| 10.8 | 15 |
| 13.0 | 19 |
| 13.3 | 17 |
| 15.2 | 13 |
| 16.3 | 12 |
| 20.4 | 12 |
| 22.9 | 35 |
| 26.4 | 12 |
| 27.2 | 16 |

The differential thermal analysis/thermogravimetry was conducted using Thermo plus TG8120 differential thermogravimetric analyzer (Rigaku, Sample amount for measurement: 3.45 mg, Heating rate: 10° C./min, Reference material: alumina). The resulting chart is shown in FIG. 2.

Endothermic peak: 75.9° C., 129.4° C.

The infrared absorption spectrum was measured using AVATAR320 (Thermo Electron) by potassium bromide disk method. The resulting spectrum chart is shown in FIG. 3. Characteristic wave numbers of infrared absorption peaks (cm$^{-1}$): 3205, 1675, 1576, 1490, 1363 and 1061

The solid-state $^{13}$C-NMR spectrum was measured using Avance DRX500 (Bruker) at the rate of 10 kHz by CP/MAS method, after the test sample was filled up in a zirconia rotor (internal diameter: 4 mm). The resulting spectrum chart is shown in FIG. 4.

Chemical shift values of the solid-state $^{13}$C-NMR (δ (ppm)): 178.9, 132.8, 102.3, 99.5, 77.7, 76.9, 76.1, 41.7, 40.9, 26.9, 25.6, 24.9, 23.4, 21.9, 21.2 and 20.0

Comparative Example 1

3-(3-{4-[3-(β-D-Glucopyanosyloxy)-5-isopropyl-1H-pyazol-4-ylmethyl]-3-methyl-phenoxy}propylamino)-2,2-dimethylpropionamide ¾ fumarate dihydrate 3-(3-{4-[3-(β-D-Glucopyanosyloxy)-5-isopropyl-1H-pyazol-4-ylmethyl]-3-methylphenoxy}propylamino)-2,2-dimethylpropionamide (1.00 g) and an equivalent of fumaric acid (0.21 g) were suspended in ethanol (15 mL), and this mixture was dissolved by heating under reflux for 5 minutes.

Toluene (7.5 mL) was added to the solution under heating, and the mixture was cooled to room temperature, and stirred overnight. After the precipitates were collected by filtration and washed with a mixed solvent of ethanol and toluene (2:1), the precipitates were dried under reduced pressure, and the crystals of the ¾ fumarate dihydrate (1.17 g) were obtained.

$^1$H-NMR (DMSO-d$_6$) (δ (ppm)): 1.04-1.10 (12H, m), 1.87-1.94 (2H, m), 2.26 (3H, s), 2.69 (2H, s), 2.72-2.75 (2H, m), 2.79 (2H, t, J=5.6 Hz), 3.08-3.21 (4H, m), 3.40-3.55 (3H, m), 3.62 (1H, d, J=10.4 Hz), 3.95 (2H, t, J=6.4 Hz), 4.40-4.50 (1H, br), 5.18 (1H, d, J=8.0 Hz), 6.50 (1.5H, s), 6.62 (1H, d, J=8.4 Hz), 6.70 (1H, s), 6.82 (1H, d, J=8.4 Hz), 6.95 (1H, s), 7.50 (1H, s), 11.25-11.75 (1H, br)

The powder X-ray diffraction of the obtained ¾ fumarate dihydrate crystals was measured under the same condition as Example 1 and the resulting diffraction diagram is shown in FIG. 5.

Test Example 1

Storage Stability Test (Deliquescence)

The hemifumarate dihydrate of Example 1, the ¾ fumarate dihydrate of Comparative Example 1 and the above compound (B) were stored under a condition of 40° C. and 75% relative humidity, and existence or nonexistence of the deliquescence was examined.

The deliquescence was observed from the initial point of the experiment in the ¾ fumarate dihydrate of Comparative Example 1 and the above compound (B) under the above condition. On the other hand, hemifumarate dihydrate of Example 1 showed no deliquescence during 2 months from the initial point of the experiment and had excellent storage stability.

Test Example 2

Storage Stability Test (Purity)

The hemifumarate dihydrate of Example 1 and the above compound (B) each were stored under a condition of 40° C. and 75% relative humidity and 60° C. in open vessels, and the storage stability for 2 months was examined. Concerning the storage stability, the purity of each test compound was measured by HPLC at initial point and after storage for 2 months, and these results were compared. Measurement conditions of HPLC are as follows.

Measurement Conditions
Detector: ultraviolet-visible absorption spectrophotometer, wavelength: 225 nm
Column: LUNA C18(2) (produced by Phenomenex), 5 μm, 4.6×250 mm, particle diameter 100×10$^{-10}$ m
Column Temperature: a constant temperature of around 25° C.
Sample concentration: 1 mg/mL
Injection volume: 10 μL
Flow rate: 1.2 mL/min
Mobile phase A: 10 mM dipotassium hydrogenphosphate aqueous solution adjusted to pH 7.8 with phosphoric acid
Mobile phase B: acetonitrile
Gradient of concentration:
  0 minute: Mobile phase B=22%
  30 minutes: Mobile phase B=22%
  50 minutes: Mobile phase B=70%
  60 minutes: Mobile phase B=70%
Range of area measurement: for 50 minutes from the start of analysis, except for the areas of the peak of fumaric acid (retention time 2 minutes), the peak of diethyl fumarate which is an impurity (retention time around 44 minutes) and the peak of the blank solution.

The results of the test under the storage condition of 40° C. and 75% relative humidity are as shown in Table 2. The decrease in the purity was observed in the above compound (B) under the above condition. On the other hand, the hemifumarate dihydrate of the present invention had excellent storage stability.

TABLE 2

| Measurement point | Example 1 The hemifumarate dihydrate (Crystals) | | The compound (B) (Amorphous material) | |
| --- | --- | --- | --- | --- |
| | Initial point | After 2 months | Initial point | After 2 months |
| Purity (%) | 99.5 | 99.6 | 98.7 | 97.0 |

The results of the test under the storage condition of 60° C. in open vessels are as shown in Table 3. The remarkable decrease in the purity due to the decomposition and coloration were observed in the above compound (B) under the high temperature environment. On the other hand, the hemifumarate dihydrate of the present invention showed almost no decrease in the purity and no coloration, and had excellent storage stability.

TABLE 3

| Measurement point | Example 1 The hemifumarate dihydrate (Crystals) | | The compound (B) (Amorphous material) | |
| --- | --- | --- | --- | --- |
| | Initial point | After 2 months | Initial point | After 2 months |
| Purity (%) | 99.5 | 99.0 | 98.7 | 95.3 |
| Appearance | White powder | White powder | White powder | Brown powder |

As described above, like the results of Test Example 1 and Test Example 2, the hemifumarate dihydrate of the present invention has extremely excellent storage stability. Thus, the hemifumarate dihydrate is an excellent compound that can solve a problem of the physicochemical properties such as the deliquescence, decrease in the purity and coloration.

INDUSTRIAL APPLICABILITY

The hemifumarate dihydrate of the present invention has excellent storage stability and other physicochemical properties. Therefore, it is useful as a drug substance and is suitable for the industrial preparation.

Figure 1:
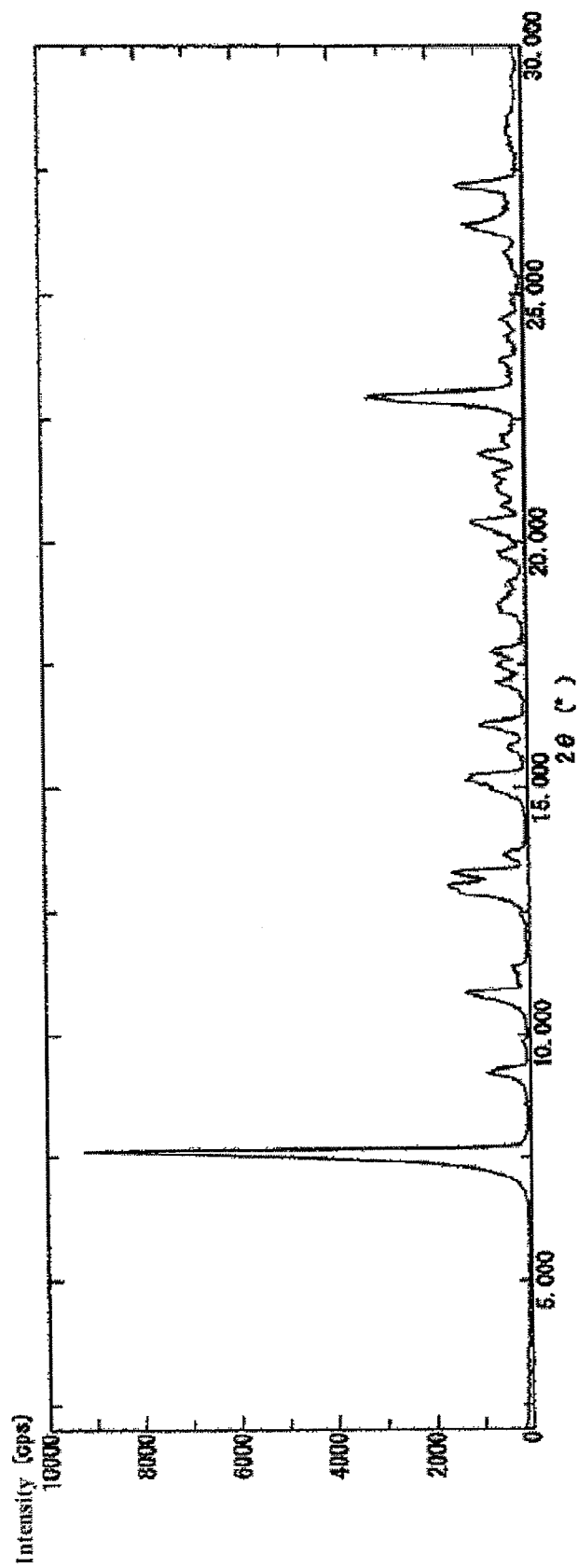
FIG. 1 is a diagram of the powder X-ray diffraction of the hemifumarate dihydrate obtained in Example 1. The axis of ordinate shows intensity of X-rays diffraction (cps), and the axis of abscissa shows diffraction angle (2θ(°)).
Figure 2:
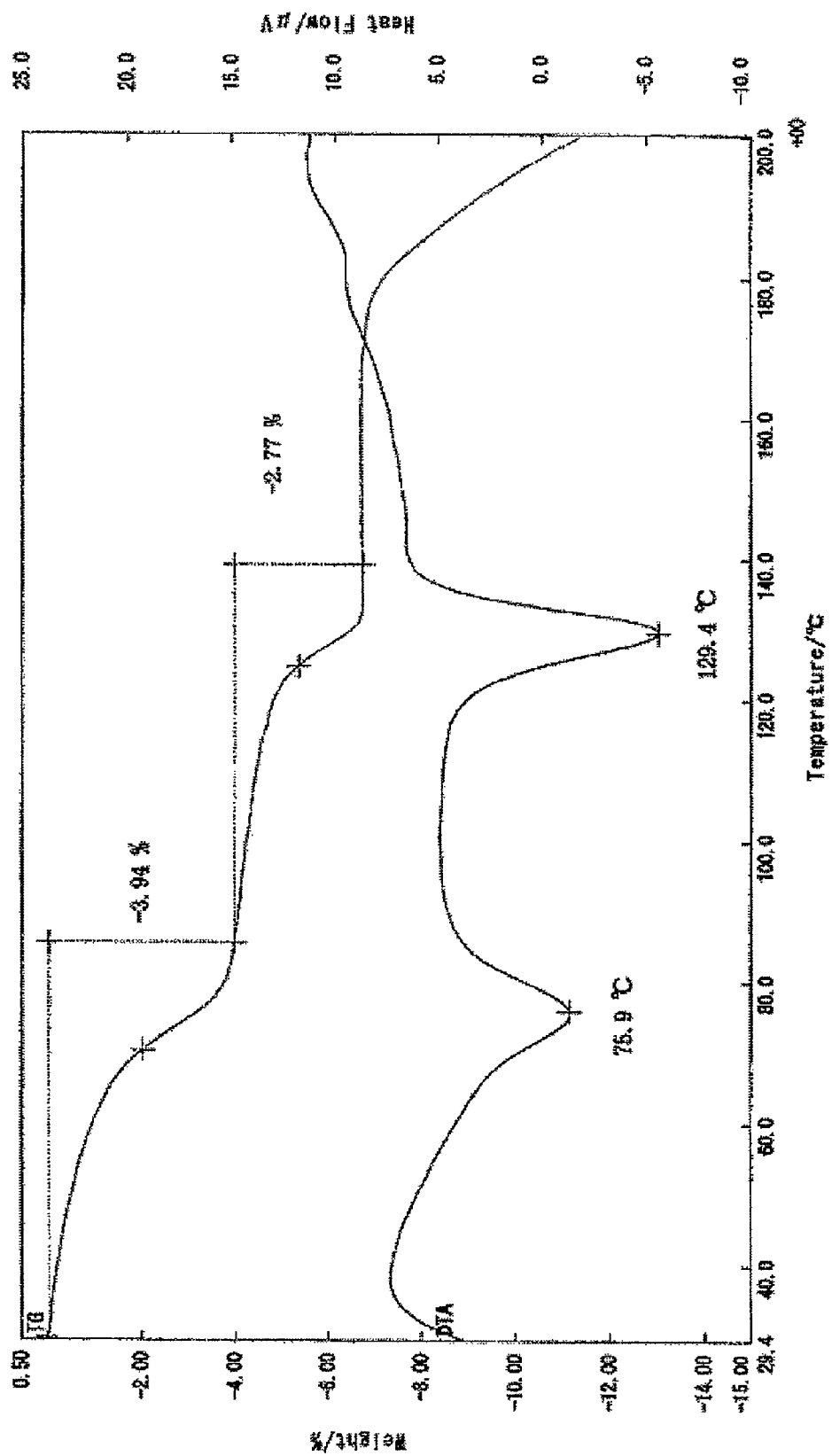
FIG. 2 is a chart of the differential thermal analysis/thermogravimetry of the hemifumarate dihydrate obtained in Example 1. The axis of ordinate shows rate of variation of weight (%) in the thermogravimetry (TG) curve and heat flow (μV) in the differential thermal analysis (DTA) curve, and the axis of abscissa shows temperature (° C.).
Figure 3:
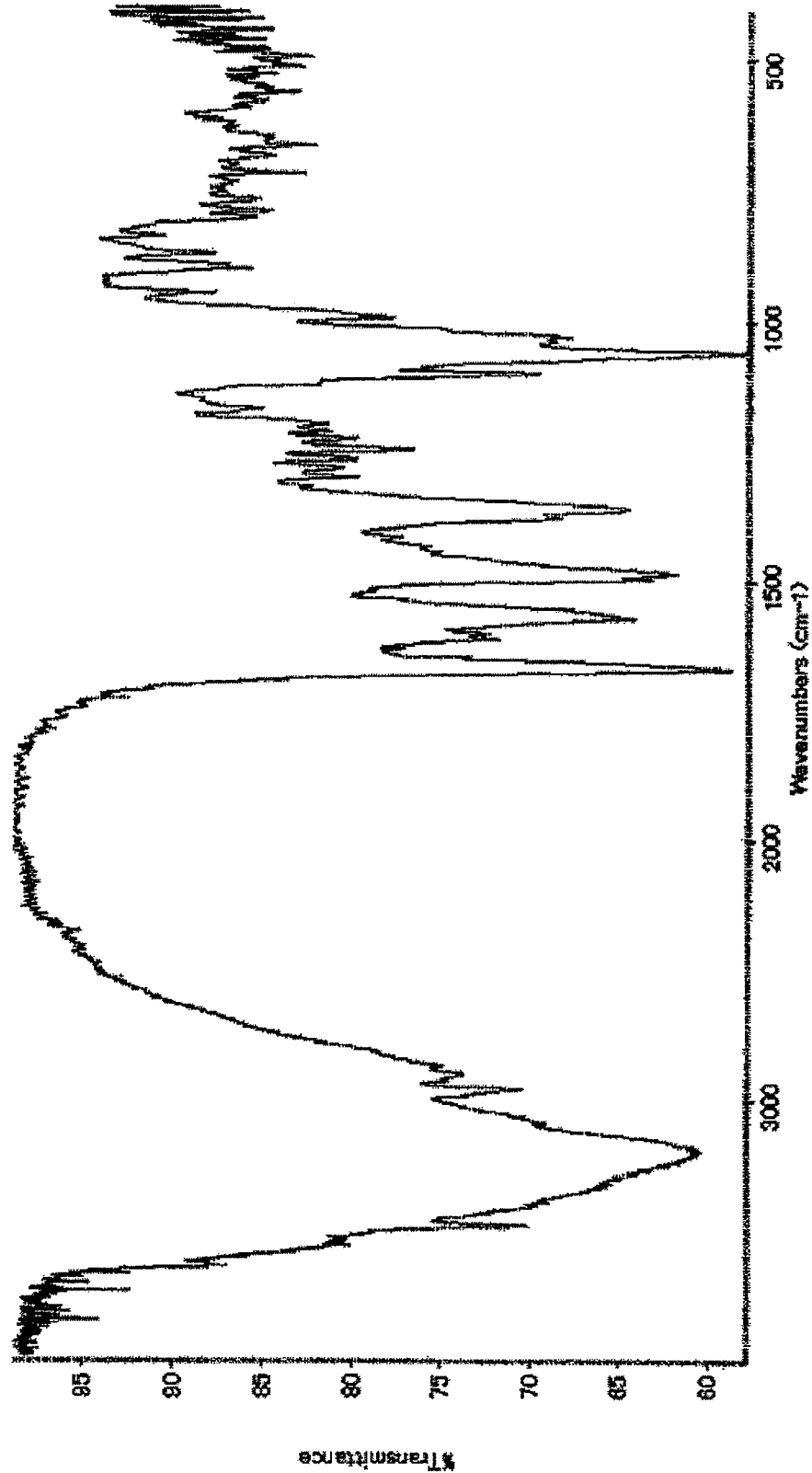
FIG. 3 is a chart of the infrared absorption spectrum of the hemifumarate dihydrate obtained in Example 1. The axis of ordinate shows transmittance (% T), and the axis of abscissa shows wave number ($cm^{-1}$).
Figure 4:
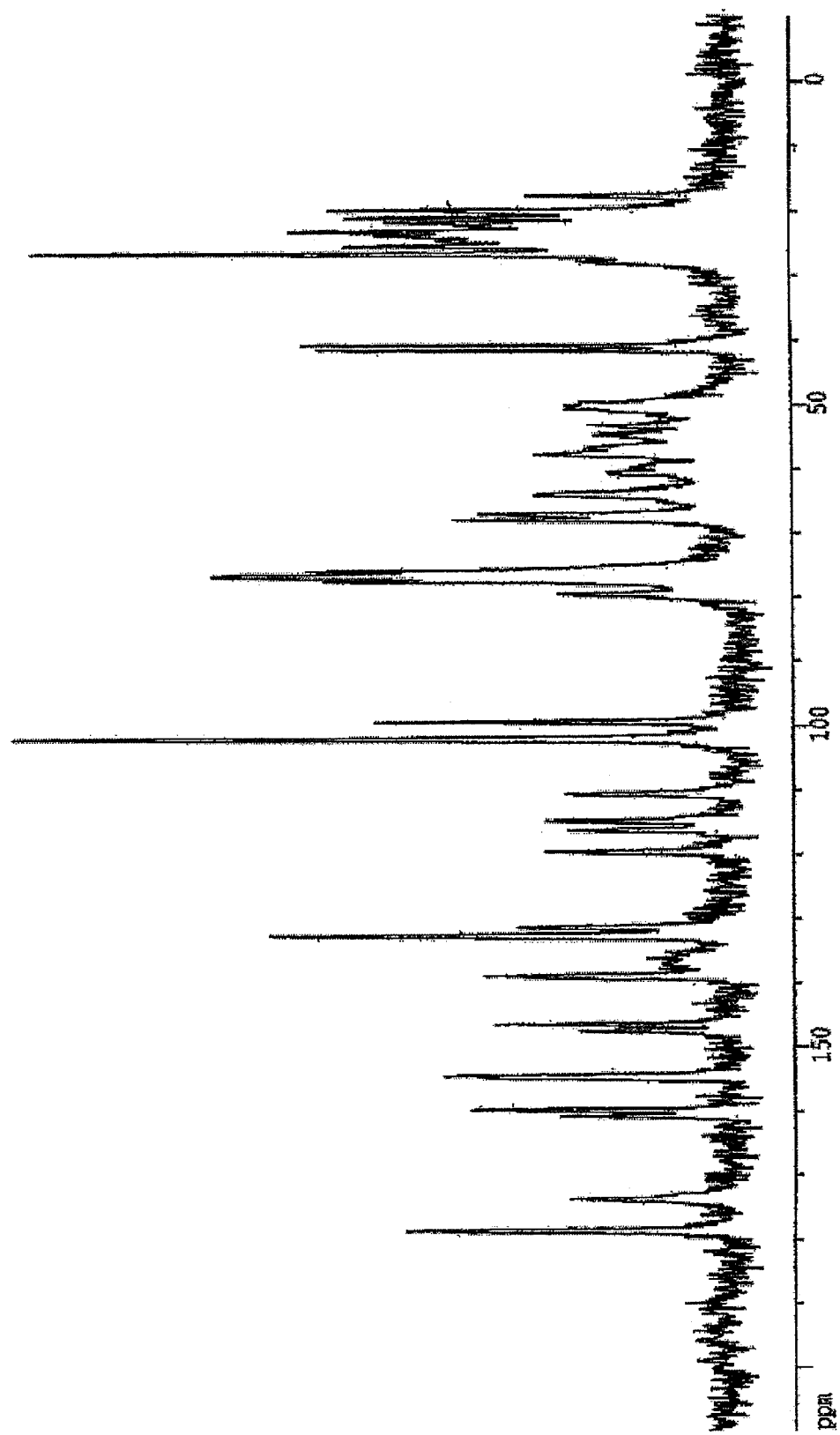
FIG. 4 is a chart of the solid-state $^{13}$C-NMR spectrum of the hemifumarate dihydrate obtained in Example 1. The axis of ordinate shows intensity, and the axis of abscissa shows chemical shift value (ppm).
Figure 5:
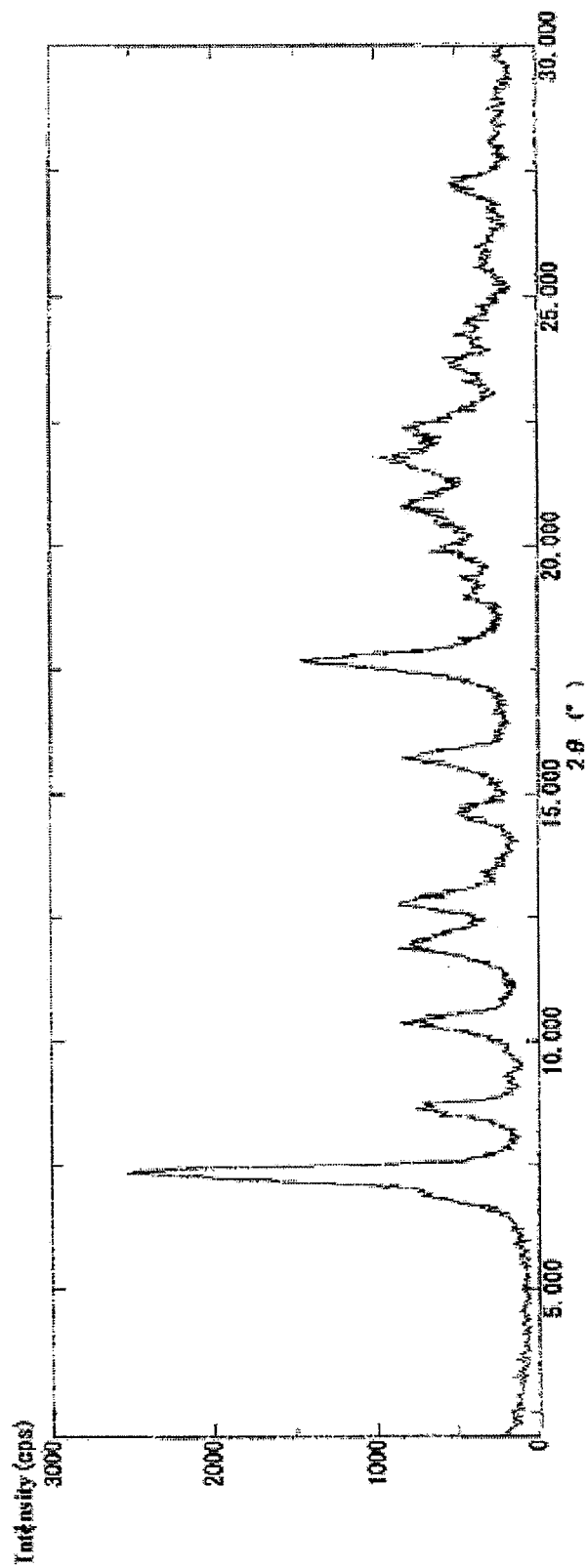
FIG. 5 is a diagram of the powder X-ray diffraction of the ¾ fumarate dihydrate obtained in Comparative Example 1. The axis of ordinate shows intensity of X-rays diffraction (cps), and the axis of abscissa shows diffraction angle (2θ(°)).

The invention claimed is:

1. A compound represented by the structural formula:

[Chem. 1]

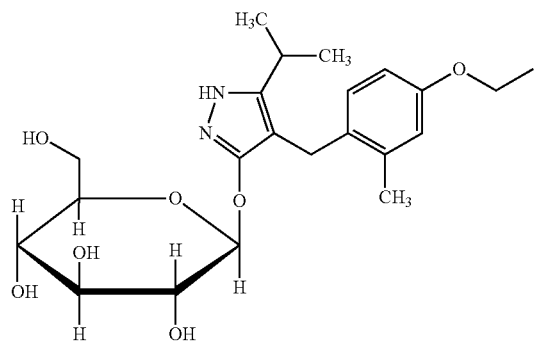

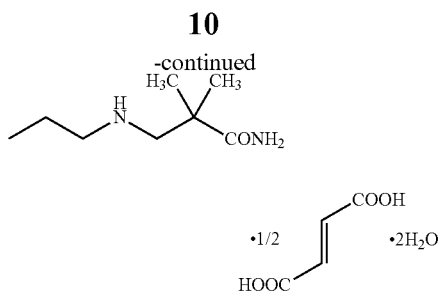

2. The compound as claimed in claim 1, which is crystalline.

3. The compound as claimed in claim 2, which has characteristic peaks at diffraction angles (2θ(°)) of 7.6±0.1, 10.8±0.1, 13.0±0.1, 13.3±0.1, 22.9±0.1 and 27.2±0.1 in a diagram of the powder X-ray diffraction.

4. The compound as claimed in claim 2, which has endothermic peaks at around 76° C. and around 129° C. in a chart of the differential thermal.

5. The compound as claimed in claim 2, which has characteristic peaks at chemical shift values (δ (ppm)) of 132.8±0.2, 102.3±0.2, 76.9±0.2 and 26.9±0.2 in a chart of the solid-state $^{13}$C-NMR spectrum.

6. A pharmaceutical composition which comprises as an active ingredient a compound as claimed in claim 1.

7. The pharmaceutical composition as claimed in claim 6 for the treatment of a disease associated with hyperglycemia or a disease associated with the increase in blood galactose level.

\* \* \* \* \*